United States Patent [19]

Drabek

[11] Patent Number: 4,511,578

[45] Date of Patent: Apr. 16, 1985

[54] ACYCLAMIDOSULFENYLCARBAMATES FOR CONTROLLING INSECTS

[75] Inventor: Jozef Drabek, Oberwil, Switzerland

[73] Assignee: Ciba-Geigy Corporation, Ardsley, N.Y.

[21] Appl. No.: 478,004

[22] Filed: Mar. 23, 1983

[30] Foreign Application Priority Data

Mar. 31, 1982 [CH] Switzerland ................. 1981/82

[51] Int. Cl.³ .................. A01N 47/24; C07D 307/86
[52] U.S. Cl. .................................. 514/469; 549/470
[58] Field of Search ................. 549/470; 424/285

[56] References Cited

U.S. PATENT DOCUMENTS 3,812,174  5/1974  Brown et al. ............... 424/300
4,006,231  2/1977  Black et al. ............... 424/248.5
4,413,005 11/1983  Goto et al. ............... 549/470

FOREIGN PATENT DOCUMENTS 2812622  9/1978  Fed. Rep. of Germany .

OTHER PUBLICATIONS

Sanzo et al., U.S. Defensive Publication No. T977,008, (12/5/78).

Primary Examiner—Nicky Chan
Attorney, Agent, or Firm—Frederick H. Rabin

[57] ABSTRACT

A composition for controlling insects, particularly for controlling insects which infest plants and animals, which composition contains, as active ingredient, a compound of the formula I

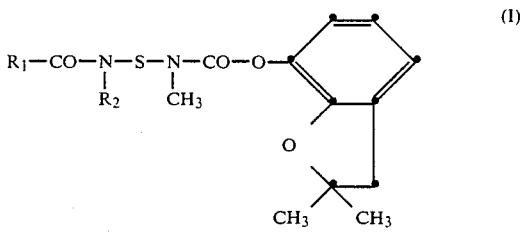

(I)

wherein $R_1$ and $R_2$ are straight-chain or branched-chain $C_1$–$C_4$-alkyl or $C_3$–$C_4$-cycloalkyl; and also processes and novel starting products for producing the compounds of the formula I.

Novel compounds of the formula Ia

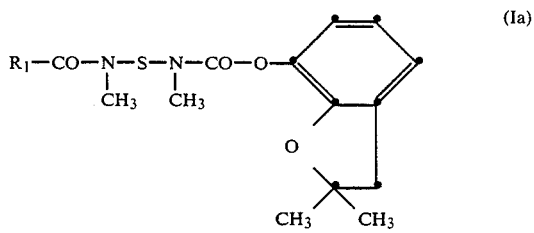

(Ia)

wherein $R_1$ is straight-chain or branched-chain $C_2$–$C_4$-alkyl or cyclopropyl.

16 Claims, No Drawings

ACYCLAMIDOSULFENYLCARBAMATES FOR CONTROLLING INSECTS

The present invention relates to insecticidal compositions containing, as insecticidal active ingredient, acylamidosulfenylcarbamates of the formula I given below, and also to the use of these carbamates for controlling insects. The invention relates also to novel active ingredients, that is, acylamidosulfenylcarbamates, which have not been described in the literature hitherto.

There is suggested according to the invention an insecticidal composition which contains, as active ingredient, a compound of the formula I

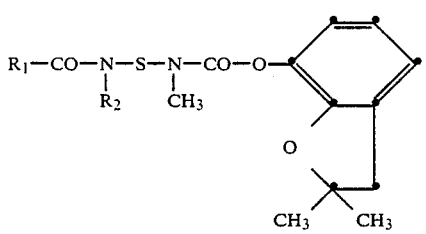

wherein $R_1$ and $R_2$ are straight-chain or branched-chain $C_1$–$C_4$-alkyl or $C_3$–$C_4$-cycloalkyl, together with suitable carriers and/or other additives.

Compositions according to the invention which are preferred on account of their action are those which contain a compound of the formula I wherein $R_1$ is straight-chain or branched-chain $C_2$–$C_4$-alkyl or $C_3$–$C_4$-cycloalkyl; and particularly those compounds wherein $R_2$ is methyl or ethyl, preferably methyl.

Compositions to be emphasised are also those which contain a compound of the formula I wherein $R_1$ is ethyl, n-propyl, isopropyl or n-butyl.

It is already known from the U.S. Pat. No. 3,812,174 that acyl-N-alkylamidosulfenyl-N'-alkylarylcarbamates have insecticidal properties. Furthermore, N-dialkylamidosulfenyl-N'-methyl-[2,2-dimethyl-2,3-dihydrobenzofuranyl (7)]-carbamates are described as pesticides, especially as insecticides, in the U.S. Pat. No. 4,006,231. Alkoxycarbonyl-N-alkylamidosulfenyl-N'-methyl-[2,2-dimethyl-2,3-dihydrobenzofuranyl (7)]-carbamates having insecticidal activity are moreover subject matter of the German Offenlegungsschrift No. 2,812,622. The compounds of the formula I stated in the foregoing as active ingredients for the compositions according to the present invention are mentioned in a general form in the U.S. Defensive Publication No. T 977 008; however, reference is made in this publication merely to the nematocidal properties of these compounds.

In the light of these findings, it has now been found that, surprisingly, the acyl-N-methylamidosulfenyl-N'-methyl-[2,2-dimethyl-2,3-dihydrobenzofuranyl (7)]-carbamates of the above formula I, which are suggested as active ingredients in the compositions according to the present invention, exhibit a good insecticidal action.

A particularly marked insecticidal action is exhibited by the compounds of the formula Ia

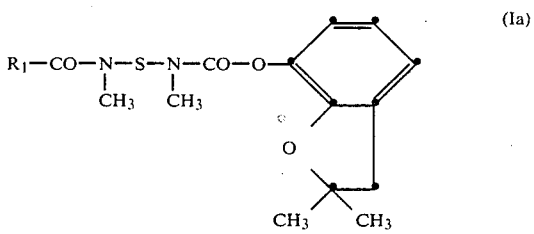

wherein $R_1$ is branched-chain or straight-chain $C_2$–$C_4$-alkyl or cyclopropyl. Preferred compounds of the formula Ia are those wherein $R_1$ is straight-chain $C_2$–$C_4$-alkyl; and also those wherein $R_1$ is ethyl, n-propyl or isopropyl.

The compounds of the formula (Ia) are novel, and are not disclosed as such in the aforementioned U.S. Defensive Publication No. T 977 008. These novel compounds likewise form subject matter of the present invention.

The compounds of the formulae I and Ia are obtainable according to the invention by application of the following novel process:

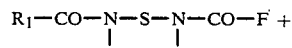

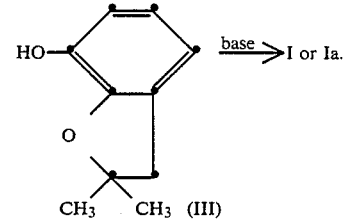

The compounds of the formulae I and Ia can be produced also by methods known per se, for example by the following procedure:

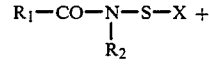

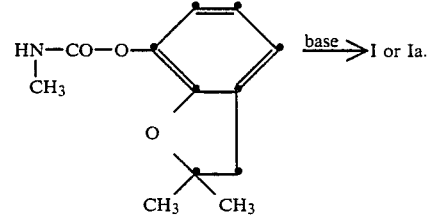

In the formulae II and IV, the symbols $R_1$ and $R_2$ have the meanings defined for the formulae I and Ia, and X is a halogen atom, especially a chlorine atom.

The processes mentioned in the foregoing are performed in general at a reaction temperature of between $-50°$ C. and $+130°$ C., preferably between $-10°$ C. and $+100°$ C., under normal or slightly elevated pressure, and preferably in the presence of a solvent or diluent which is inert to the reactants.

Suitable bases for these processes are in particular tertiary amines, such as trialkylamines, pyridines and dialkylanilines, also hydroxides, oxides, carbonates and bicarbonates of alkali metals and alkaline-earth metals, as well as alkali metal alcoholates, for example potassium tert-butylate and sodium methylate.

Suitable solvents or diluents are for example: ethers and ethereal compounds, such as diethyl ether, di-isopropyl ether, dioxane or tetrahydrofuran; aliphatic and aromatic hydrocarbons, especially benzene, toluene or xylenes; and ketones, such as acetone, methyl ethyl ketone and cyclohexanone.

The starting materials of the formulae III to V are known, or in cases where they are novel, they can be produced by methods analogous to known methods (cp. for example: U.S. Pat. No. 3,320,286, U.S. Defensive Publication No. T 977 008 and British Patent Specification No. 999.128). The starting materials of the formula II are novel compounds and they too form subject matter of the present invention.

The compounds of the formulae I and Ia, and the compositions containing them, are suitable, inter alia, for controlling insects of the orders: Lepidoptera, Coleoptera, Homoptera, Heteroptera, Diptera, Thysanoptera, Orthoptera, Anoplura, Siphonaptera, Mallophaga, Thysanura, Isoptera, Psocoptera and Hymenoptera.

It is to be emphasised that the stated compounds according to the invention are characterised by both a strongly pronounced systemic action and contact action against sucking insects, especially against sucking insects of the order Homoptera, and above all against insects of the family Aphididae (for example Aphis fabae, Aphis craccivora and Myzus persicae), all of which can be controlled with known compositions only with great difficulty. Besides having a favourable action against mosquito larvae, compounds of the formulae I and Ia can also be used for controlling insects which damage plants by eating, in crops of ornamental plants and productive plants, especially in cotton crops (for example against Anthonomus grandis, Spodoptera littoralis and Heliothis virescens); and also in fruit and vegetable crops (for example against Laspeyresia pomonella, Leptinotarsa decemlineata and Epilachna varivestis). The compounds of the formulae I and Ia are distinguished moreover by a good action against larval insect stages and nymphs, especially against insects which damage plants by eating. To be mentioned also is the broad ovicidal and ovolarvicidal action of compounds of the formulae I and Ia. When compounds of the formulae I and Ia are taken up with the feed by adult insect stages, there is observed in many cases, especially with Coleoptera, for example Anthonomus grandis, a reduced oviposition and/or a lessened rate of hatching. Furthermore, the compounds of the formulae I and Ia can be successfully used against Chilo suppressalis, and against plant-damaging cicadas, such as *Laodelphax striatellus* and *Nilaparvata lugens*, particularly in rice crops.

The compounds of the formula I and Ia are suitable also for controlling ectoparasites, such as Lucilia sericata, in both domestic and productive animals, for example by treatment of animals, livestock housing and pasture land.

The action of the compounds of the formulae I and Ia, and also of the compositions containing them, can be considerably broadened and adapted to suit given circumstances by the addition of other insecticides and/or acaricides. Suitable additives are for example the following active ingredients: organic phosphorus compounds, nitrophenols and derivatives thereof, formamidines, ureas, carbamates, chlorinated hydrocarbons and *Bacillus thuringiensis* preparations.

The compounds of the formulae I and Ia can be combined with particular advantage also with substances which intensify pesticidal activity. Examples of compounds of this type are, inter alia: piperonylbutoxide, propynyl ethers, propynyl oximes, propynyl carbamates and propynyl phosphonates, 2-(3,4-methylenedioxyphenoxy)-3,6,9-trioxaundecane or S,S,S-tributylphosphorotrithioates.

The good insecticidal action of the stated compounds of the formulae I and Ia according to the present invention corresponds to a mortality rate (mortality) of at least 50–60% of the harmful insects mentioned.

The compounds of the formulae I and Ia are used either in an unmodified form or preferably together with auxiliaries customarily employed in formulation practice, and are thus processed, in a known manner, for example into the form of emulsion concentrates, directly sprayable or dilutable solutions, diluted emulsions, wettable powders, soluble powders, dusts or granulates, and also encapsulations in for example polymeric substances. The application processes, such as spraying, atomising, dusting, scattering or pouring, and likewise the type of composition, are selected to suit the objectives to be achieved and the given conditions.

The formulations, that is to say, the compositions or preparations containing the active ingredient of the formula I or Ia, or combinations of this active ingredient with other insecticides or acaricides, and optionally a solid or liquid additive, are produced in a known manner, for example by the intimate mixing and/or grinding of the active ingredient with extenders, such as with solvents, solid carriers and optionally surface-active compounds (tensides).

Suitable solvents are: aromatic hydrocarbons, preferably the fractions $C_8$ to $C_{12}$, such as xylene mixtures or substituted naphthalenes, phthalic esters, such as dibutyl- or dioctylphthalate, aliphatic hydrocarbons, such as cyclohexane or paraffins, alcohols and glycols, as well as ethers and esters thereof, such as ethanol, ethylene glycol, ethylene glycol monomethyl or -ethyl ethers, ketones such as cyclohexanone, strongly polar solvents, such as N-methyl-2-pyrrolidone, dimethylsulfoxide or dimethylformamide, as well as optionally epoxidised vegetable oils, such as epoxidised coconut oil or soybean oil; or water.

The solid carriers used, for example for dusts and dispersible powders, are as a rule natural mineral fillers, such as calcite, talcum, kaolin, montmorillonite or attapulgite. In order to improve the physical properties, it is also possible to add highly dispersed silicic acids or highly dispersed absorbent polymers. Suitable granulated adsorptive carriers are porous types, for example pumice, ground brick, sepiolite or bentonite; and suitable nonsorbent carriers are materials such as calcite or sand. A great number of pre-granulated materials of inorganic or organic nature, such as in particular dolomite or ground plant residues, can also be used.

Suitable surface-active compounds are, depending on the nature of the active ingredient of the formula I or Ia, or of the combination of this active ingredient with other insecticides or acaricides, to be formulated: nonionic, cationic and/or anionic tensides having good emulsifying, dispersing and wetting properties. By 'tensides' are also meant mixtures of tensides.

Suitable anionic tensides are both so-called water-soluble soaps, as well as water-soluble, synthetic, surface-active compounds.

Soaps which may be mentioned are the alkali metal, alkaline-earth metal or optionally substituted ammonium salts of higher fatty acids ($C_{10}$–$C_{22}$), for example the sodium or potassium salts of oleic or stearic acid, or of natural fatty acid mixtures, which can be obtained for example from coconut oil or tallow oil. Also to be mentioned are the fatty acid-methyl-taurine salts, as well as modified and unmodified phospholipides.

So-called synthetic tensides are however more frequently used, particularly fatty sulfonates, fatty sulfates, sulfonated benzimidazole derivatives or alkylarylsulfonates. The fatty sulfonates or sulfates are, as a rule, in the form of alkali metal, alkaline-earth metal or optionally substituted ammonium salts, and they generally contain an alkyl group having 8 to 22 C atoms, 'alkyl' including also the alkyl moiety of acyl groups, for example the Na or Ca salt of ligninsulfonic acid, of dodecylsulfuric acid ester or of a fatty alcohol sulfate mixture produced from natural fatty acids. Included among these are the salts of sulfuric acid esters and sulfonic acids of fatty alcohol ethylene oxide adducts. The sulfonated benzimidazole derivatives preferably contain 2 sulfonic acid groups and a fatty acid group having about 8–22 C atoms. Alkylarylsulfonates are for example the Na, Ca or triethanolamine salts of dodecylbenzenesulfonic acid, of dibutylnaphthalenesulfonic acid or of a naphthalenesulfonic acid-formaldehyde condensation product. Also suitable are corresponding phosphates, for example salts of the phosphoric ester of a p-nonylphenol-(4–14)-ethylene oxide adduct, Suitable nonionic tensides are in particular polyglycol ether derivatives of aliphatic or cycloaliphatic alcohols, saturated or unsaturated fatty acids and alkylphenols, which can contain 3 to 30 glycol ether groups and 8 to 20 carbon atoms in the (aliphatic) hydrocarbon radical and 6 to 18 carbon atoms in the alkyl moiety of the alkylphenols. Further suitable nonionic tensides are the water-soluble polyethylene oxide adducts, which contain 20 to 250 ethylene glycol ether groups and 10 to 100 propylene glycol ether groups, with polypropylene glycol, ethylenediaminopolypropylene glycol and alkylpolypropylene glycol having 1 to 10 carbon atoms in the alkyl chain. The compounds mentioned usually contain 1 to 5 ethylene glycol units per propylene glycol unit. Examples of nonionic tensides which may be mentioned are: nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol. Suitable also are fatty acid esters of polyoxyethylenesorbitan, such as polyoxyethylenesorbitan-trioleate.

In the case of the cationic tensides, they are in particular quaternary ammonium salts which contain as N-substituents at least one alkyl group having 8 to 22 C atoms and, as further substituents, lower, optionally halogenated alkyl, benzyl or lower hydroxyalkyl groups. The salts are preferably in the form of halides, methyl sulfates or ethyl sulfates, for example stearyltrimethyl ammonium chloride or benzyldi-(2-chloroethyl)-ethylammonium bromide.

The tensides customarily used in formulation practice are described, inter alia, in the following publication:

"Mc Cutcheon's Detergents and Emulsifiers Annual" MC Publishing Corp., Ringwood, N.J., 1979.

The pesticidal preparations contain as a rule 0.1 to 99%, particularly 0.1 to 95%, of active ingredient of the formula I or Ia, or of combinations of this active ingredient with other insecticides or acaricides, 1 to 99.9% of a solid or liquid additive, and 0 to 25%, especially 0.1 to 20%, of a tenside. Whereas commercial products are preferably in the form of concentrated compositions, the products employed by the end-user are as a rule preparations having considerably lower concentrations of active ingredient.

The compositions can also contain additives such as stabilisers, antifoaming agents, viscosity regulators, binders and adhesives, as well as fertilisers or other active ingredients for obtaining special effects.

Formulation examples for liquid active ingredients of the formula I or Ia, or combinations of these active ingredients with other insecticides or acaricides
(%=percent by weight)

| 1. Emulsion concentrates | (a) | (b) | (c) |
|---|---|---|---|
| active ingredient or active ingredient combination | 25% | 40% | 50% |
| calcium dodecylbenzenesulfonate | 5% | 8% | 6% |
| castor-oil-polyethylene glycol ether (36 mols of ethylene oxide) | 5% | — | — |
| tributylphenol-polyethylene glycol ether (30 mols of ethylene oxide) | — | 12% | 4% |
| cyclohexanone | — | 15% | 20% |
| xylene mixture | 65% | 25% | 20% |

Emulsions of any required concentration can be produced from such concentrates by dilution with water.

| 2. Solutions | (a) | (b) | (c) | (d) |
|---|---|---|---|---|
| active ingredient or active ingredient combination | 80% | 10% | 5% | 95% |
| ethylene glycol monomethyl ether | 20% | — | — | — |
| polyethylene glycol MG 400 | — | 70% | — | — |
| N—methyl-2-pyrrolidone | — | 20% | — | — |
| epoxidised coconut oil | — | — | 1% | 5% |
| ligroin (boiling limits 160–190° C.) | — | — | 94% | — |

The solutions are suitable for application in the form of very fine drops.

| 3. Granulates | (a) | (b) |
|---|---|---|
| active ingredient or active ingredient combination | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| 4. Dusts | (a) | (b) |
|---|---|---|
| active ingredient or active ingredient combination | 2% | 5% |
| highly dispersed silicic acid | 1% | 5% |
| talcum | 97% | — |
| kaolin | — | 90% |

Ready-for-use dusts are obtained by the intimate mixing together of the carriers with the active ingredient.

Formulation examples for solid active ingredients of the formula I or Ia, or combinations of these active ingredients with other insecticides or acaricides
(% = percent by weight)

| 5. Wettable powders | (a) | (b) | (c) |
|---|---|---|---|
| active ingredient or active ingredient combination | 25% | 50% | 75% |
| sodium lignin sulfonate | 5% | 5% | — |
| sodium lauryl sulfate | 3% | — | 5% |
| sodium diisobutylnaphthalene sulfonate | — | 6% | 10% |
| octylphenolpolyethylene glycol ether (7–8 mols of ethylene oxide) | — | 2% | — |
| highly dispersed silicic acid | 5% | 10% | 10% |
| kaolin | 62% | 27% | — |

The active ingredient or the active ingredient combination is well mixed with the additives, and the mixture is thoroughly ground in a suitable mill. Wettable powders which can be diluted with water to give suspensions of the required concentration are obtained.

| 6. Emulsion concentrate | |
|---|---|
| active ingredient or active-ingredient combination | 10% |
| octylphenol polyethylene glycol ether (4–5 mols of ethylene oxide) | 3% |
| calcium dodecylbenzene sulfonate | 3% |
| castor oil polyglycol ether (36 mols of ethylene oxide) | 4% |
| cyclohexanone | 30% |
| xylene mixture | 50% |

Emulsions of the required concentration can be obtained from the concentrate by dilution with water.

| 7. Dusts | (a) | (b) |
|---|---|---|
| active ingredient or active ingredient combination | 5% | 8% |
| talcum | 95% | — |
| kaolin | — | 92% |

Dusts ready for use are obtained by mixing the active ingredient with the carrier and grinding the mixture in a suitable mill.

| 8. Extruder granulate | |
|---|---|
| active ingredient or active-ingredient combination | 10% |
| sodium lignin sulfonate | 2% |
| carboxymethylcellulose | 1% |
| kaolin | 87% |

The active ingredient is mixed and ground with the additives, and the mixture is moistened with water. This mixture is extruded, granulated, and subsequently dried in a stream of air.

| 9. Coated granules | |
|---|---|
| active ingredient or active-ingredient combination | 3% |
| polyethylene glycol (MG 200) | 3% |
| kaolin | 94% |

The finely ground active ingredient or the active-ingredient combination is evenly applied, in a mixer, to the kaolin moistened with polyethylene glycol. Dust-free coated granules are obtained in this manner.

| 10. Suspension concentrate | |
|---|---|
| active ingredient or active-ingredient combination | 40% |
| ethylene glycol | 10% |
| nonylphenol-polyethylene glycol (15 mols of ethylene oxide) | 6% |
| sodium lignin sulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient or the active-ingredient combination is intimately mixed with the additives. There is thus obtained a suspension concentrate from which can be prepared, by dilution with water, suspensions of the concentration required.

EXAMPLE 1: PRODUCTION OF THE STARTING COMPOUNDS 200 ml of toluene are placed into a polyethylene apparatus and cooled to $-50°$ C. In the toluene at this temperature are dissolved, with stirring, 13.2 g of hydrofluoric acid, and to this solution are then added dropwise at $-50°$ to $-30°$ C., in the course of 15 minutes, 39.1 ml of methylisocyanate. The reaction mixture is stirred for a further 2 hours, and is afterwards diluted with 800 ml of toluene. To this solution are added dropwise, during 10 minutes, 100.6 g of N-chlorosulfenylpropionic acid methylamide, and subsequently at $-10°$ C., within 30 minutes, 90.9 ml of triethylamine. The reaction mixture is then stirred for 24 hours at room temperature, and for 8 hours at $50°-60°$ C. and, after cooling, the mixture is filtered with suction. The resulting filtrate is concentrated by evaporation, and the residue obtained is distilled under high vacuum. There is thus obtained the compound of the formula $$CH_3-CH_2-CO-N-S-N-CO-F,$$
$$\quad\quad\quad\quad\quad\quad\ \ |\quad\ \ |$$
$$\quad\quad\quad\quad\quad\quad CH_3\ \ CH_3$$

b.p. 78–83° C./0.07–0.1 Torr.

The following compounds of the formula II are produced in a corresponding manner:

| $R_1$ | $R_2$ | Physical data |
|---|---|---|
| $CH_3-$ | $CH_3-$ | b.p. 64–70° C./0.05 Torr |
| $CH_3-(CH_2)_2-$ | $CH_3-$ | b.p. 96–98° C./0.08 Torr |
| $(CH_3)_2CH-$ | $CH_3-$ | b.p. 82–87° C./0.08 Torr |
| $CH_3-(CH_2)_3-$ | $CH_3-$ | |
| $CH_3-CH_2-CH(CH_3)-$ | $CH_3-$ | |
| $(CH_3)_3C-$ | $CH_3-$ | |
| $(CH_3)_2CH-CH_2-$ | $CH_3-$ | |
| $\begin{array}{c}CH_2\\ \ \ \ \diagdown\\ \quad\quad CH-\\ \ \ \ \diagup\\ CH_2\end{array}$ | $CH_3-$ | |

Production of isobutyryl-N-methylamidosulfenyl-N'-methyl-[2,2-dimethyl-2,3-dihydrobenzofuranyl(7)]carbamate 11.0 g of isobutyryl-N-methylamidosulfenyl-N'-methylcarbamoyl fluoride in 10 ml of toluene are added dropwise at a temperature of 0° to 10° C., during 20 minutes, to a solution of 8.67 ml of 2,2-dimethyl-2,3-dihydro-7-hydroxybenzofuran, 11.05 ml of triethylamine and 0.2 g of dimethylaminopyridine in 100 ml of toluene. The reaction mixture is stirred for 5 hours at room temperature, and then for 12 hours at 70° to 80° C. After the organic solvent has been distilled off, the reaction mixture is taken up in toluene, and successively washed, in the separating funnel, with 100 ml of water, 100 ml of 1N hydrochloric acid, 100 ml of 1N sodium bicarbonate solution and 100 ml of 20% sodium chloride solution. The separated organic phase is dried over sodium sulfate, and the solvent is distilled off. There is thus obtained, as distillation residue, the title compound in the form of an oil, $n_D^{40} = 1.5260$, of the formula (compound No. 1)

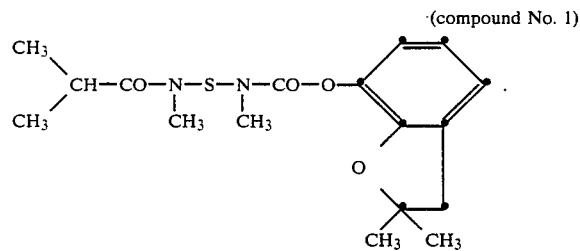

The following compounds of the formula I or Ia are obtained by a procedure analogous to that described in the foregoing,

| Compound No. | $R_1$ | $R_2$ | Physical data |
|---|---|---|---|
| 2 | $CH_3-(CH_2)_2-$ | $CH_3-$ | $n_D^{40} = 1.5278$ |
| 3 | $CH_3-CH_2-$ | $CH_3-$ | $n_D^{45} = 1.5380$ |
| 4 | $CH_3-(CH_2)_3-$ | $CH_3-$ | $n_D^{30} = 1.5280$ |
| 5 | $CH_3-CH_2-CH(CH_3)-$ | $CH_3-$ | |
| 6 | $(CH_3)_3C-$ | $CH_3-$ | |
| 7 | $(CH_3)_2CH-CH_2-$ | $CH_3-$ | |
| 8 | $\begin{array}{c}CH_2\\ \phantom{CH_2}\diagdown\\ \phantom{CH_2}\phantom{X}CH-\\ \phantom{CH_2}\diagup\\ CH_2\end{array}$ | $CH_3$ | |

EXAMPLE 2: ACTION AGAINST AEDES AEGYPTI

Sufficient of a 0.1% acetonic solution of the active ingredient concerned is transferred by pipette to the surface of 150 ml of water in a container to obtain concentrations of 800 and 400 ppm in each case. After the acetone has been evaporated off, 30–40 two-day-old Aëdes larvae are placed into each container. The mortality rate is ascertained after 1, 2 and 5 days.

Compounds of the formula I and Ia, respectively, according to Example 1 exhibit in this test a good action against Aedes aegypti.

EXAMPLE 3: INSECTICIDAL CONTACT ACTION AGAINST APHIS CRACCIVORA

Pea seedlings grown in water are each infested before commencement of the test with about 200 individuals of the Aphis craccivora species. The plants infested in this manner are sprayed dripping wet 3 days later, from a distance of 30 cm, with solutions containing 3.0 and 0.75 ppm, respectively, of the compounds to be tested. Two plants are used per test compound and per concentration, and an evaluation of the mortality rate achieved is made after a further 24 hours.

EXAMPLE 4: INSECTICIDAL SYSTEMIC ACTION AGAINST MYZUS PERSICAE

Rooted radish plants are transplanted to pots each containing 600 ccm of soil; and the plants are subsequently infested with a population of Myzus persicae. After 3 days, 50 ml of an aqueous preparation of the compound to be tested (obtained from a 25% emulsifiable wettable powder), at a concentration of 3.0 and 12.5 ppm, respectively, are then poured directly onto the soil in each case. The test is carried out in a greenhouse at 28° C., and two plants, each in a separate pot, are used per concentration level and per test substance. An evaluation of the mortality rate achieved is made 48 hours after application of the aqueous preparation.

EXAMPLE 5: INSECTICIDAL STOMACH-POISON ACTION AGAINST LASPEYRESIA POMONELLA

Apples of the 'Golden Delicious' variety are sprayed with aqueous emulsion-preparations containing 3.0, 12.5, 50, 100 and 200 ppm, respectively, of the compound to be tested. After the applied coating has dried, larvae of the species Laspeyresia pomonella ($L_1$ stage) are settled onto the fruit, each apple receiving two test insects. Two apples are used per test compound, and the test is carried out at 25° C. with 60% relative humidity. An evaluation of the mortality rate achieved is made after 4 days.

EXAMPLE 6: ACTION ON LASPEYRESIA POMONELLA (EGGS)

Deposited Laspeyresia pomonella eggs, not more than 24 hours old, are immersed on filter paper for 1 minute in an acetonic/aqueous solution containing 12.5, 200 and 400 ppm, respectively, of the active ingredient to be tested. After the solution has dried on the eggs, they are laid out in Petri dishes and are kept at a temperature of 28° C. The percentage hatching rate from the treated eggs is assessed after 6 days.

EXAMPLE 7: ACTION ON HELIOTHIS VIRESCENS (EGGS)

Appropriate proportions of a wettable, pulverulent formulation containing 25 percent by weight of the active ingredient to be tested are mixed with specific amounts or water to give aqueous emulsions of increasing concentration of active ingredient, that is, 12.5, 50, 100 and 400 ppm. One-day-old clusters of eggs of Heliothis deposited on cellophane are immersed for three minutes in the above respective emulsions containing the active ingredient to be tested, and are then filtered by suction on round filters. The egg clusters treated in this manner are subsequently laid out in Petri dishes and kept in darkness. After 6 to 8 days, the hatching rate compared with that of untreated control clusters is determined. The criterion for the evaluation is the minimum concentration of active ingredient required to effect a 100% destruction of the eggs.

EXAMPLE 8: ACTION AGAINST *ANTHONOMUS GRANDIS*

Two potted cotton plants in the 6-leaf stage are sprayed with aqueous emulsion preparations capable of wetting, and containing 50, 100 and 400 ppm, respectively, of the active ingredient to be tested. After the drying of the applied coating (about one and a half hours), 10 adult beetles (*Anthonomus grandis*) are settled onto each plant. A plastics cylinder, the upper opening of which is covered with gauze, is placed over each treated plant infested with the test insects, for the purpose of preventing the beetles from escaping. The treated plants are kept at 25° C. with about 60% relative humidity. An evaluation is made after 2, 3, 4 and 5 days with respect to the percentage mortality rate of the test beetles (% dorsal position), and also with respect to the antifeeding effect, in each case compared with that occurring with untreated control groups.

EXAMPLE 9: EFFECT ON REPRODUCTION OF *ANTHONOMUS GRANDIS*

Adult *Anthonomus grandis*, which have been hatched no longer than 24 hours, are transferred, in groups each of 25 beetles, to cages having lattice walls. The cages containing the beetles are then immersed for 5 to 10 seconds in an acetonic solution containing 1.0 percent by weight of the active ingredient to be tested. After the beetles are again dry, they are placed, for copulation and oviposition, into covered dishes containing feed. Deposited eggs are flushed out with running water two or three times weekly; they are then counted, disinfected by being placed for two to three hours into an aqueous disinfectant, and are subsequently deposited into dishes containing a suitable larval diet. An examination is made after 7 days to determine whether larvae have developed from the deposited eggs.

In order to ascertain the duration of the reproduction-influencing effect of the active ingredients tested, the oviposition of the beetles is observed during a period of about four weeks. The evaluation is on the basis of the reduction in the number of eggs deposited and larvae hatched in comparison with that in the case of untreated control specimens.

Compounds of the formula I and Ia, respectively, according to Example 1 exhibit a good reproduction-reducing effect in the above test.

EXAMPLE 10: ACTION AGAINST *LAODELPHAX STRIATELLUS* AND *NILAPARVATA LUGENS* (NYMPHS)

The test is carried out on growing plants. For this purpose, 4 rice plants (thickness of stem 8 mm) having a height of about 20 cm are planted in pots (diameter 8 cm). The plants are sprayed, on a rotary table, with in each case 100 ml of an acetonic solution containing 50, 200, 400 and 800 ppm, respectively, of active ingredient. After the applied coating has dried, each plant is infested with 20 nymphs of the test insects in the third stage. In order to prevent the cicadas from escaping, a glass cylinder is place over each infested plant, and the upper opening of the cylinder is covered with gauze. The nymphs are kept on the treated plant for about 10 days until they have reached the next development stage. An evaluation with respect to % mortality is made 1, 4 and 8 days after the treatment.

Compounds of the formula I and Ia exhibit a high level of activity against nymphs of Laodelphax striatellus and Nilaparvata lugens.

EXAMPLE 11: ACTION AGAINST *LAODELPHAX STRIATELLUS* AND *NILAPARVATA LUGENS* (OVICIDAL)

The test is carried out on growing plants. In each case, 4 rice plants (thickness of stem 8 mm, height about 20 cm) are planted in pots (diameter 8 cm). The plants are sprayed, on a rotary table) with in each case 100 ml of an acetonic solution containing 400 and 800 ppm, respectively, of active ingredient. After the applied coating has dried, 3 adult females are settled onto each plant. In order to prevent the insects from escaping, a glass cylinder is placed over each infested plant, and the upper opening of the cylinder is covered with gauze. The females remain 4 days until oviposition on the treated plant, and are then removed. The young cicadas have hatched about 8 days after infestation, and are then counted. The percentage mortality rate is assessed on the basis of a comparison of the number of hatched larvae on the treated plants with the number of hatched larvae on the untreated control plants.

Compounds of the formula I and Ia according to Example 1 exhibit in the above test a good ovicidal action.

BIOLOGICAL RESULTS

The following Table shows results of insecticidal tests on compounds according to the invention on the basis of the above biological Examples. The criterion used for evaluating the test results is the % mortality rate achieved, the evaluation index used being as follows:

A: 80–100% mortality rate at a concentration of 0.75 ppm of the compound tested;
B: 80–100% mortality rate at a concentration of 3.0 ppm of the compound tested;
C: 80–100% mortality rate at a concentration of 12.5 ppm of the compound tested;
D: 80–100% mortality rate at a concentration of 50 ppm of the compound tested;
E: 80–100% mortality rate at a concentration of 100 ppm of the compound tested;
F: 80–100% mortality rate at a concentration of 200 ppm of the compound tested; and
G: 80–100% mortality rate at a concentration of 400 ppm of the compound tested.

| Compound No. | Insecticidal activity | | | | | | |
|---|---|---|---|---|---|---|---|
| | Aphis craccivora-direct spray (Example 3) | Myzus persicae-systemic (Example 4) | Laspeyresia pomonella-larvae (Example 5) | Laspeyresia pomonella-eggs (Example 6) | Heliothis virescens-eggs (Example 7) | Anthonomus grandis-adults (Example 8) | Laodelphax striatellus-nymphs (Example 10) |
| 1 | A | C | C | C | D | E | D |
| 2 | A | C | D | C | C | E | D |
| 3 | — | — | D | — | — | G | D |

-continued

| | Insecticidal activity | | | | | | |
|---|---|---|---|---|---|---|---|
| Compound No. | Aphis craccivora- direct spray (Example 3) | Myzus persicae- systemic (Example 4) | Laspeyresia pomonella- larvae (Example 5) | Laspeyresia pomonella- eggs (Example 6) | Heliothis virescens- eggs (Example 7) | Anthonomus grandis- adults (Example 8) | Laodelphax striatellus- nymphs (Example 10) |
| 4 | — | B | B | F | D | D | — |

What is claimed is:

1. A compound of the formula

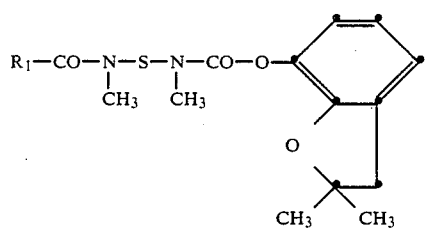

wherein $R_1$ is straight-chain or branched-chain $C_2-C_4$-alkyl or cyclopropyl.

2. A compound according to claim 1, wherein $R_1$ is straight-chain $C_2-C_4$-alkyl.

3. A compound according to claim 1, wherein $R_1$ is ethyl, n-propyl or isopropyl.

4. A compound according to claim 3 of the formula

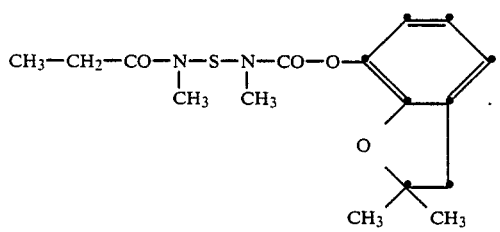

5. A compound according to claim 3 of the formula

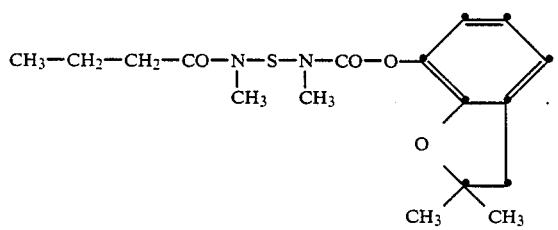

6. A compound according to claim 3 of the formula

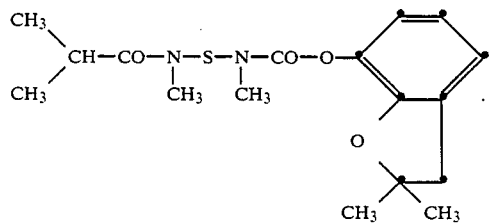

7. A compound according to claim 2 of the formula

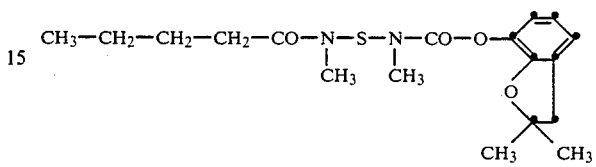

8. A composition for controlling insects, which composition contains as active ingredient of an insecticidally effective amount of a compound according to claim 1 together with suitable carriers and/or other additives.

9. A composition according to claim 1 in which the compound $R_1$ is ethyl, n-propyl, isopropyl or n-butyl.

10. A composition according to claim 9, which contains as active ingredient the compound of the formula

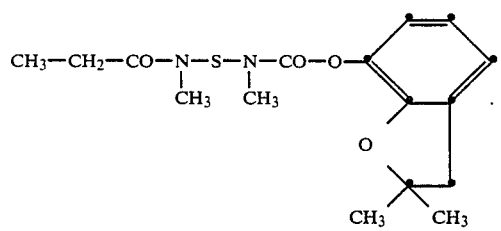

11. A composition according to claim 9, which contains as active ingredient the compound of the formula

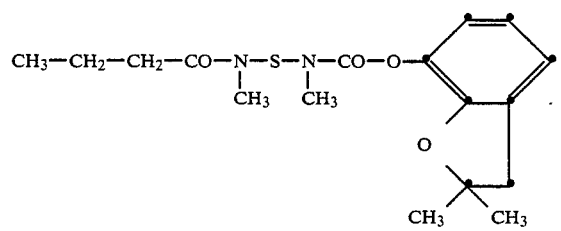

12. A composition according to claim 9, which contains as active ingredient the compound of the formula

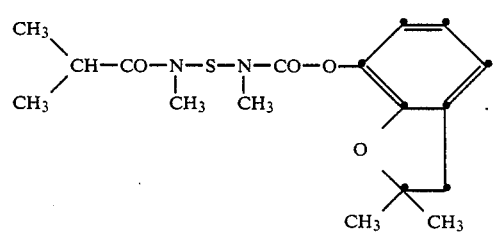

13. A composition according to claim 9, which contains as active ingredient the compound of the formula

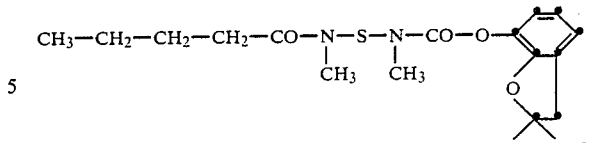

14. A method of controlling insects, which method comprises applying thereto or to the locus thereof an insecticidally effective amount of a compound according to claim 1.

15. A method according to claim 14 for controlling insects which damage plants.

16. A method according to claim 15 for controlling eggs and/or larval stages of insects which damage plants.

* * * * *

UNITED STATES PATENT AND TRADEMARK OFFICE
CERTIFICATE OF CORRECTION

PATENT NO. : 4,511,578
DATED : April 16, 1985
INVENTOR(S) : Jozef Drabek

It is certified that error appears in the above-identified patent and that said Letters Patent is hereby corrected as shown below:

Claim 8, Column 14, Line 22 should read-- position contains as active ingredient an insecticid- --.

Signed and Sealed this

Twenty-second Day of October 1985

[SEAL]

Attest:

DONALD J. QUIGG

Attesting Officer

Commissioner of Patents and
Trademarks—Designate